United States Patent [19]

Hanck et al.

[11] Patent Number: 4,514,338
[45] Date of Patent: Apr. 30, 1985

[54] PANTHENOL DERIVATIVES

[75] Inventors: Alfred Hanck, Riehen; Horst Pauling, Bottmingen, both of Switzerland

[73] Assignee: Hoffmann-La Roche Inc., Nutley, N.J.

[21] Appl. No.: 461,093

[22] Filed: Jan. 26, 1983

[30] Foreign Application Priority Data

Feb. 12, 1982 [CH] Switzerland ............................ 890/82

[51] Int. Cl.³ ............................................... C07F 5/06
[52] U.S. Cl. ................................................. 260/429.9
[58] Field of Search ........................ 260/448 R, 429.9

[56] References Cited

FOREIGN PATENT DOCUMENTS 840839 6/1952 Fed. Rep. of Germany.

OTHER PUBLICATIONS

The Merck Index of Chemicals and Drugs, 7th Edition, p. 770, (1960).
Rompps Chemie-Lexikon, 8th Ed., pp. 157 & 571, 2491–2493, 3990–3991, (1979).
Pharmacie, 33(11), pp. 765–766, (1978).
Chemical Abstracts, 90, 43882q, (1979).

*Primary Examiner*—Helen M. S. Sneed
*Attorney, Agent, or Firm*—Jon S. Saxe; Bernard S. Leon; George W. Johnston

[57] ABSTRACT

Aluminium panthenolate and zinc panthenolate, their manufacture and use as topical medicaments are described.

5 Claims, No Drawings

PANTHENOL DERIVATIVES

SUMMARY OF THE INVENTION

The present invention is concerned with panthenol derivatives. More particularly, the invention is concerned with novel salts of panthenol, namely aluminium D- or DL-panthenolate and zinc D- or DL-panthenolate.

The invention is also concerned with the manufacture of these compounds and their use as topical medicaments for promoting the healing of wounds.

DETAILED DESCRIPTION OF THE INVENTION

The invention is concerned with panthenol derivatives. These compounds have the formula:
D or DL

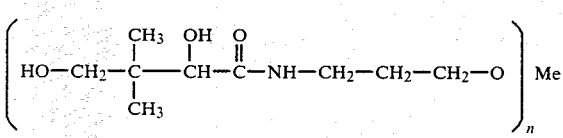   I wherein
Me is aluminium and n is the integer 3, or
Me is zinc and n is the integer 2.

The invention is also concerned with the manufacture of the compounds of formula I and their use as topical medicaments.

The compounds of formula I can be manufactured by reacting D- or DL-panthenol of the formula

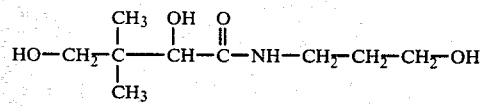   II with a compound of the formula

   III (R)$_2$AlH   IV wherein
R is a $C_1$–$C_{12}$-alkyl or $C_1$–$C_{12}$-alkoxy group,
in the molar ratio 3:1 or with a compound of the formula

   V wherein
R is as above,
in the molar ration 2:1.

In the specification the terms "alkyl" or "$C_1$–$C_{12}$alkyl" signify straight-chain and branched-chain alkyl groups containing 1 to 12 carbon atoms, preferably those containing 2–8 carbon atoms. Typical examples are ethyl, propyl, isopropyl, n-butyl, isobutyl, tert butyl, pentyl, hexyl etc. Triisobutylaluminium is an especially preferred alkylaluminium compound and diethylzinc is an especially preferred alkylzinc compound. The term "lower alkyl" signifies alkyl moieties containing 1–6 carbon atoms.

The terms "alkoxy" or "$C_1$–$C_{12}$-alkoxy" signify alkoxy groups in which the alkyl residue has the significance given above. The compounds of formulae III-V in which R signifies alkoxy are alcoholates, there being preferred those which are derived from alcohols having a boiling point below 118°–120° C. at $10^{-2}$ Torr. Aluminium isopropylate and zinc isopropylate are preferred alcoholates.

The reaction of D- or DL-panthenol with a compound of formulae III-V in which R signifies alkyl can conveniently be carried out in an aprotic anhydrous solvent and under a dry protective gas such as nitrogen or argon. Suitable solvents are, for example, aliphatic hydrocarbons such as hexane or heptane, aromatic hydrocarbons such as benzene or toluene, chlorinated hydrocarbons such as methylene chloride or chlorobenzene, ethers such as diethyl ether or anisole and the like. The reaction generally proceeds rapidly and quantitatively. Since the hydrocarbons and the hydrogen formed are either gases or low-boiling liquids, these can be separated readily. When pure starting materials are used, the reaction proceeds in one step directly to analytically pure products which do not require further purification.

For the manufacture of aluminium D-panthenolate, D-panthenol is preferably reacted with triisobutylaluminium. For the manufacture of the DL-form, DL-panthenol is used as the starting material. In place of triisobutylaluminium there can also be used a bis(lower alkyl)aluminium hydride compound, preferably diisobutylaluminium hydride.

For the manufacture of zinc D-panthenolate, D-panthenol is preferably reacted with diethylzinc. For the manufacture of the DL-form, DL-panthenol is used as the starting material.

The reaction of D- or DL-panthenol with a compound of formulae III-V in which R signifies alkoxy comprises reacting an alcoholate of aluminium or of zinc with the panthenol. Thereby, such alcohol ROH is displaced by the panthenol and this proceeds especially well when the alcohol to be displaced has a boiling point lower than that of panthenol. In this process there can likewise be used the previously mentioned solvents, but it is advantageous to carry out the reaction in a solvent which forms an azeotrope with the alcohol ROH which is to be removed from the reaction mixture. When pure starting materials are used, analytically pure end products are obtained directly in this manner in one reaction step after separation of the alcohol ROH and the solvent.

For the manufacture of aluminium D-panthenolate, D-panthenol is preferably reacted with aluminium isopropylate. For the manufacture of zinc D-panthenolate, D-panthenol is preferably reacted with zinc isopropylate. For the manufacture of the DL-forms DL-panthenol is used as the starting material.

The starting materials used in the process provided by the invention are either known and, in part, can be purchased in sufficient purity or can be prepared in an analogous manner to the known compounds.

The compounds of formula I provided by the invention, which have been found to have a very low toxicity in mice, come into consideration as topical medicaments. The compounds of formula I have been found to be practically non-irritating to the skin and to be non-allergic in guinea pigs, which is an extraordinarily favorable characteristic for a topical medicament to possess.

The topical medicaments provided by the invention especially enhance the healing of soft tissue (e.g. skin, mucous membrane) wounds in mammals. The term "wounds" includes surgical incisions, abrasions, scratches, lacerations, cuts, punctures, ulcers, fissures, tears, sores, blisters, burns, ruptures and the like.

More specifically, the inventive medicaments promote the healing and epithelization of wounds. For example, the medicaments are useful in treating burns, scratches and cuts, chronic ulcers, bedsores and anal fissures and for after-treatment following skin transplants and operative measures in the case of cervix erosions. The compounds provided by the invention are also suitable for the prophylaxis and therapy of anticipatable wounds such as cracked nipples, diaper or napkin rash and sunburn. Furthermore, it has been shown that the tensile strength of operation scars increases significantly when the compound provided by the invention are used. Quite generally, when the compounds provided by the invention are used a more rapid and better healing of wounds is achieved. It has also been established that the compounds provided by the invention have an inhibiting effect on the growth of suppurative organisms. That is, they have an antiseptic activity, and surprisingly at the same time they bring about an activation of the macrophages.

Although the D- or DL-forms can be used in accordance with the invention, the D-isomers of the inventive compounds are preferred.

In accordance with the invention, one or more compounds of formula I are applied topically to the soft tissue of a mammal at the site of the wound. The compounds of formula I are conveniently used in the form of pharmaceutical preparations or compositions which contain an effective amount of compound I and a pharmaceutically acceptable carrier material which is suitable for topical administration to the wound site. Topical dosage forms provided by the invention generally contain about 0.1 to 10 weight percent, preferably 0.5 to 5 weight percent, of a compound of formula I, based on the total weight of the dosage form. However, higher or lower concentrations can also be present depending on the dosage form which is used. The inventive topical preparations can be applied to the wound site in an amount and under a time schedule varying with the needs of the patient. For example, the preparations can be applied to the wound site once or twice a day or more often, if needed.

The term "topical" as used in the present specification relates to the use of the active ingredient of formula I, which is processed with a suitable carrier material and which is applied to the skin or mucous membrane, so that it can display local activity. Accordingly, the topical medicaments embrace pharmaceutical dosage forms which are suitable for external use, so that a direct contact with the skin results. The topical dosage forms embrace gels, creams, lotions, salves, powders, aerosols and other conventional forms which are suitable for the direct application of medicaments to the skin or mucous membrane. These dosage forms can be manufactured by mixing compound of formula I with known pharmaceutical carrier materials which are suitable for topical use.

Salves and creams contain oily, absorbent, water-soluble and/or emulsifying carrier materials such as vaseline, paraffin oil, propylene glycol, cetyl alcohol, glycerine monostearate, alkyl-branched fatty acids and the like.

Lotions are liquid preparations and can vary from simple solutions to aqueous or aqueous/alcoholic preparations which contain the substances in finely divided form. The preparations contain suspending or dispersing substances such as, for example, sodium carboxymethylcellulose which suspend or disperse the active substance in a carrier prepared from water, alcohol, glycerine and the like.

Gels are semi-solid preparations which are obtained by gelling a solution or suspension of the active substance in a carrier material. The carrier materials, which can be hydrophilic or hydrophobic, are gelled using a gelling agent such as Carbopol and the like.

Aerosols are solutions or suspensions of the active substance in an inert carrier material which are applied using spray generators. Usually used carriers are trichloromonofluoromethane and trichlorodifluoromethane.

The following examples further illustrate the invention. Unless indicated otherwise, temperature is expressed in degrees Celsius (°C.) and the examples were performed and compositions were prepared as written. Neo-PCL and Neo-PCL (water soluble) are preparations made by Dragoco located at Holzminden, Germany. Aerosil 200 is silicon dioxide manufactured by Degussa, Frankfurt, Germany.

EXAMPLE 1

72.8 g (354.7 mmol) of D-panthenol and 400 ml of absolute dichloromethane are added at room temperature under an inert gas to a 1 liter four-necked flask provided with a powerful stirrer, 250 ml dropping funnel with pressure balance and reflux condenser, as well as an apparatus for working under a protective gas. Since the D-panthenol dissolves poorly in dichloromethane, the mixture is stirred very vigorously and cooled to 50° C. in an ice-bath. To this emulsion there are added dropwise within 1 hour 23.46 g (30.0 ml, 118.2 mmol) of tri-isobutylaluminium dissolved in 150 ml of absolute toluene. A white stirrable mass is thereby obtained. After completion of the addition, the mixture is left to warm to room temperature, then warmed to 60° C. (bath temperature) and the dichloromethane is distilled off. The mixture is then heated for 2 hours at the reflux temperature of the toluene. After cooling to about 50° C., the toluene is removed under a water-jet vacuum and the residue is dried up to constant weight under an oil pump vacuum. The residue is dried for 24 hours at 50° C. in a vacuum drying oven under an oil pump vacuum, the product thereby gradually becoming solid. After cooling, the colourless amorphous mass can be pulverized in a mortar to a white powder which is slightly hydgroscopic. There are obtained 73.24 g of aluminium D-panthenolate having a melting interval of 78°–82° C. and a specific rotation of $[\alpha]_D^{20} = +47.8°$ (c=1 in dimethyl sulphoxide).

EXAMPLE 2

(a) 9.1 ml (7.1 g; about 118.3 mmol) of absolute isopropanol and 300 ml of absolute n-hexane are added to a 500 ml three-necked flask, provided with a dropping funnel, stirrer and apparatus for working under a protective gas, and the mixture is cooled to about 5° C. A solution of 10 ml (7.82 g; about 39.4 mmol) of triisobutylaluminium in 60 ml of absolute n-hexane is added dropwise while stirring well. Thereafter, the cooling bath is removed and the temperature in the reaction flask is allowed to come to room temperature. The mixture is then warmed at 50° C. for 2 hours. In this manner there is obtained a clear solution of aluminium isopropylate in n-hexane.

(b) 24.3 g (118.3 mmol) of D-panthenol are placed in a similar apparatus so that described in paragraph (a). Thereto there is added the aluminium isopropylate solution in n-hexane prepared as described in paragraph (a). The mixture is stirred at room temperature for 2 hours and heated under reflux for 4 hours. Thereafter, n-hexane and isopropanol are distilled off at normal pressure. From the dropping funnel there is added absolute n-hexane (about 300 ml) until isopropanol can no longer be detected by gas chromatography in the distillate. The remaining hexane is then removed during 2 hours, firstly under normal pressure and finally (at about 65° C. heating bath temperature) in an oil pump vacuum, there being obtained 25.2 g of aluminium D-panthenolate.

EXAMPLE 3

58.90 g (287 mmol) of D-panthenol and 600 ml of n-hexane (purest) are added at room temperature under an inert gas to a 1 liter four-necked flask, provided with a stirrer, 100 ml dropping funnel with pressure balance and reflux condenser as well as an apparatus for working under a protective gas, and the mixture is stirred vigorously. The D-panthenol is difficulty soluble in n-hexane. When the D-panthenol has emulsified to small droplets, there are added dropwise from the dropping funnel within 1 hour 17.73 g (15.0 ml; 143.5 mmol) of diethylzinc diluted in 80 ml of n-hexane (purest). The reaction begins immediately and is recognizable by the escape of ethane; the batch warms slightly. After about a third of the diethylzinc solution has been added, the reaction flask contains a viscous difficultly stirrable mass. After cooling to 5° C. in an ice-bath, the mass becomes solid and it is then pulverized to a fine powder. The mixture is left to come slowly to room temperature and the dropwise addition is continued. After completion of the addition, the mixture is warmed to reflux temperature, stirred at this temperature for 1 hour, again left to cool to room temperature and stirred overnight. Thereafter, 250 ml of n-hexane are distilled off and the mixture remaining is cooled to 5° C. in an ice-bath and left to stand without stirring for 2 hours. The product solidifies and the n-hexane can be decanted off well. The remainder of the n-hexane is removed under a water-jet vacuum and then the residue is dried up to constant weight under an oil pump vacuum. Since the product is hygroscopic, it is stored with the exclusion of moisture. There are obtained 60.73 g of zinc D-panthenolate in the form of a white amorphous powder having a melting interval of 105°–107° C. and a specific rotation of $[\alpha]_D^{20} = +31°$ (c=1% in dimethyl sulphoxide).

EXAMPLE 4

(a) A solution of 11.5 g (14.75 ml, about 191.4 mmol) of absolute isopropanol in 300 ml of absolute n-hexane is placed under argon in a 500 ml four-necked flask, provided with stirrer, thermometer, dropping funnel, as well as a reflux condenser with an apparatus for working under a protective gas, and the mixture is cooled to 5° C. Thereto there is slowly added dropwise a solution of 10 ml (11.82 g; about 95.7 mmol) of diethylzinc in 60 ml of absolute n-hexane. After completion of the addition, the mixture is warmed to 50° C. for 2 hours.

(b) 39.3 g (191.4 mmol) of D-panthenol are added at room temperature to the suspension of zinc isopropylate in n-hexane prepared as described in paragraph (a). n-Hexane and isopropanol are distilled off at normal pressure while stirring, fresh n-hexane (about 300 ml) being added until isopropanol can no longer be detected by gas chromatography in the distillate. The residual solvent is then removed, firstly in a water jet pump vacuum and then during 2 hours in an oil pump vacuum, and the residue is dried up to constant weight, there being obtained 42.9 g of zinc D-panthenolate.

EXAMPLE A

A wound gel in a neutral gel base having the following composition is manufactured in a manner known per se:

Zinc D-panthenolate—5.0 g
Glycofurol—9.0 g
Isopropyl alcohol—11.0 g
Neo-PCL—68.0 g
Aerosil 200—7.0 g

EXAMPLE B

A wound gel in a neutral gel base having the following composition is manufactured in a manner known per se:

Aluminium D-penthenolate—5.0 g
Glycofurol —9.0 g
Isopropyl alcohol—12.0 g
Neo-PCL—68.0 g
Aerosil 200—6.0 g

EXAMPLE C

A salve has the following composition:
Aluminium D-panthenolate—1.0 g
Glycofurol—9.0 g
Miglyol gel—90.0 g A representative batch is manufactured as follows:
1 g of aluminium D-panthenolate is dissolved in 9.0 g of glycofurol and the solution is mixed with 10.0 g of Miglyol gel (Miglyol gel is a pharmaceutical adjuvant consisting of a triglyceride mixture of saturated vegetable fatty acids).

EXAMPLE D

A gel has the following composition:
Aluminium D-panthenolate—1.0 g
Glycofurol—9.0 g
Isopropyl alcohol—12.0 g
Neo-PCL (water-soluble)—72.0 g
Aerosil 200—6.0 g A representative batch is manufactured as follows:
1 g of aluminium D-panthenolate is dissolved in 9.0 g of glycofurol and the solution is mixed with 12.0 g of isopropyl alcohol. This mixture is added to 72.0 g of Neo-PCL (water-soluble) and finally 6.0 g of Aerosil 200 are added under stirring.

EXAMPLE E

A powder has the following composition:
Aluminium D-panthenolate—25.0 g
Magnesium stearate—2.36 g
Talc—64.75 g
Zinc oxide 7.89 g A representative batch is manufactured as follows:
25.0 g of aluminium D-panthenolate are sieved through a sieve (0.5 mm) together with 2.36 g of magnesium stearate, 64.75 g of talc and 7.89 g of zinc oxide and the mixture obtained is mixed for 15 minutes in a mixer.

EXAMPLE F

A powder has the following composition:
Zinc D-panthenolate—5.0 g

Magnesium stearate—3.0 g

Talc—82.0 g

Zinc oxide—10.0 g

A representative batch is manufactured as follows:

5 g of zinc D-panthenolate are sieved through a sieve (0.5 mm) together with 3.0 g of magnesium stearate, 82 g of talc and 10 g of zinc oxide and the mixture obtained is mixed for 15 minutes in a mixer.

We claim:

1. A compound of the formula D or DL

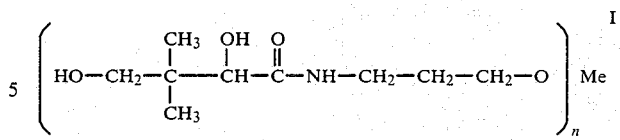

wherein
Me is aluminium and n is the integer 3 or Me is zinc and
n is the integer 2.

2. The compound of claim 1 wherein Me is aluminium and n is the integer 3.

3. The compound of claim 2, aluminium D-panthenolate.

4. The compound of claim 1 wherein Me is zinc and n is the integer 2.

5. The compound of claim 4, zinc D-panthenolate.

* * * * *